United States Patent
Baba et al.

(10) Patent No.: US 8,419,900 B2
(45) Date of Patent: *Apr. 16, 2013

(54) APPARATUS FOR PRETREATMENT FOR SACCHARIFICATION OF LIGNOCELLULOSE BIOMASS

(75) Inventors: Tsuyoshi Baba, Saitama (JP); Shigenobu Mitsuzawa, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 20 days.

This patent is subject to a terminal disclaimer.

(21) Appl. No.: 13/126,138

(22) PCT Filed: Nov. 11, 2009

(86) PCT No.: PCT/JP2009/006011
§ 371 (c)(1),
(2), (4) Date: Apr. 26, 2011

(87) PCT Pub. No.: WO2010/055647
PCT Pub. Date: May 20, 2010

(65) Prior Publication Data
US 2011/0203757 A1   Aug. 25, 2011

(30) Foreign Application Priority Data
Nov. 13, 2008   (JP) ................. 2008-291400

(51) Int. Cl.
*D21C 7/10* (2006.01)
(52) U.S. Cl.
USPC ........................................ 162/250
(58) Field of Classification Search ......... 162/250, 162/239; 435/72, 289.1; 127/36, 37
See application file for complete search history.

(56) References Cited

U.S. PATENT DOCUMENTS

| 7,144,552 | B1 * | 12/2006 | Fukuizumi et al. | 422/62 |
| 2011/0239685 | A1 * | 10/2011 | Baba | 62/324.1 |
| 2012/0012266 | A1 * | 1/2012 | Baba et al. | 162/239 |

FOREIGN PATENT DOCUMENTS

| JP | 2001-179063 A | 7/2001 |
| JP | 2005-232453 A | 9/2005 |
| JP | 2005-288320 A | 10/2005 |
| JP | 2007-275889 A | 10/2007 |

OTHER PUBLICATIONS

Kim Tae Hyun. et al., "Pretreatment and fractionation of corn stover by ammonia recycle percolation process", Bioresource Technology, 2005, vol. 96, p. 2007-2013.

Sendich Elizabeth Newton. et al., "Recent process improvements for the ammonia fiber expansion (AFEX) process and resulting reductions in minimum ethanol selling price", Bioresources Technology, Apr. 28, 2008, vol. 99, p. 8429-8435.

* cited by examiner

*Primary Examiner* — Mark Halpern
(74) *Attorney, Agent, or Firm* — Arent Fox LLP

(57) ABSTRACT

To provide an apparatus for pretreatment for saccharification easily and continuously applying a treatment and capable of reusing ammonia at low cost. The apparatus has a mixing unit 2, a first heating unit 3, a separation unit 4, a transfer unit 6, an ammonia water supply unit 8 and an ammonia recovery unit 19. The apparatus may have the first heat exchanger 18, a second heat exchanger 25 and a heat supply unit 27 and further has a second heating unit 14. The apparatus may have a wet grinding unit 32 between the heating unit 3 and 25.

6 Claims, 4 Drawing Sheets

APPARATUS FOR PRETREATMENT FOR SACCHARIFICATION OF LIGNOCELLULOSE BIOMASS

CROSS-REFERENCE TO RELATED APPLICATION

This application is a National Stage entry of International Application No. PCT/JP2009/006011, filed Nov. 11, 2009, which claims priority to Japanese Application No. 2008-291400, filed Nov. 13, 2008, the entire specification claims and drawings of which are incorporated herewith by reference.

TECHNICAL FIELD

The present invention relates to an apparatus for pretreatment for saccharification of lignocellulose biomass for use in producing bioethanol.

BACKGROUND ART

Recently, in view of preventing global warming, it has been required to reduce emissions of carbon-dioxide, which is considered as one of the causes. Then, it has been investigated to use a blended fuel of liquid hydrocarbon such as gasoline and ethanol as fuel for motor vehicles.

As the ethanol of the blended fuel, if bioethanol obtained by fermentation and distillation of a plant substance e.g., an agriculture product, such as sugar cane and corn is used, it is considered that a so-called carbon neutral effect can be obtained. The carbon neutral effect means that if a substance derived from a plant is used as bioethanol, when the ethanol is burned the net carbon dioxide emission theoretically becomes zero. This is because the amount of carbon dioxide discharged in the air by combustion of bioethanol is equal to the amount of carbon dioxide absorbed by a plant itself serving as a raw material from the air.

Therefore, if bioethanol is used in place of liquid hydrocarbon such as gasoline, carbon-dioxide emissions can be reduced by the amount of bioethanol.

However, if sugar cane, corn and the like are used as a raw material for ethanol in a large amount, the amount of them supplied as food reduces. This is a problem.

Then, a technique for producing ethanol by using nonedible lignocellulose biomass in place of a plant substance such as sugar cane and corn has been investigated. The lignocellulose biomass contains cellulose. If the cellulose is decomposed by enzymatic saccharification into glucose and the obtained glucose is fermented, bioethanol can be obtained. Examples of the lignocellulose biomass include wood, rice straw, wheat straw, bagasse, bamboo, pulp and waste materials (e.g., used paper) produced from these.

However, lignocellulose contains hemicellulose and lignin other than cellulose as major components. Usually cellulose and hemicellulose are tightly bound with lignin. As the result, an enzymatic saccharification reaction to cellulose is inhibited by lignin. Thus, to perform the enzymatic saccharification reaction of cellulose, lignin is desirably removed in advance.

For this purpose, an apparatus for pretreatment for saccharification of lignocellulose biomass is known in which the lignocellulose biomass is mixed with liquid ammonia and then the pressure is rapidly reduced to expand gas of liquid ammonia, thereby expanding the biomass to remove lignin from the biomass (see, for example, Patent Literature 1).

Such a conventional apparatus for pretreatment for saccharification of lignocellulose biomass has a mixing unit, a heating unit, a discharge means and a recovery unit.

In the conventional apparatus for pretreatment for saccharification of lignocellulose biomass, lignocellulose biomass and liquid ammonia are mixed by the mixing unit to obtain a biomass-ammonia mixture. Subsequently, the biomass-ammonia mixture is heated by the heating unit and ammonia is discharged while being pressurized and compressed by the discharge means so as not to evaporate ammonia. The biomass-ammonia mixture, if treated in this manner, is rapidly reduced in pressure after discharge and liquid ammonia explosively expands. As a result, the biomass rapidly expands to remove lignin bound to the biomass. Furthermore, the ammonia gas recovery unit separates ammonia gas from the biomass-ammonia mixture discharged by the discharge means and recovers the ammonia gas.

CITATION LIST

Patent Literature

Patent Literature 1: Japanese Patent Laid-Open No. 2005-232453

SUMMARY OF INVENTION

Technical Problem

However, the conventional apparatus for pretreatment for saccharification of lignocellulose biomass has a disadvantage. Since the biomass-ammonia mixture is treated at a high temperature and high pressure, a continuous treatment is not easily performed. Furthermore, to reuse ammonia gas separated by the separation unit as liquid ammonia, the ammonia gas must be pressurized to about 2 MPa. Cost disadvantageously increases.

An object of the present invention is to provide an apparatus for pretreatment for saccharification of lignocellulose biomass easily and continuously applying a treatment by overcoming these disadvantages and capable of reusing ammonia at low cost.

Solution to Problem

To attain the object, an apparatus for pretreatment for saccharification of lignocellulose biomass of the present invention has a mixing unit which mixes lignocellulose biomass and ammonia, a first heating unit which heats a biomass-ammonia mixture provided by the mixing unit, a separation unit which separates ammonia gas from the biomass-ammonia mixture heated by the first heating unit to obtain a biomass-water mixture, and a transfer unit which transfers the biomass-water mixture separated by the separation unit to a later step, further having an ammonia water supply unit which supplies ammonia water to the mixing unit and an ammonia recovery unit which recovers ammonia gas as ammonia water by dissolving ammonia gas separated by the separation unit in water.

According to the apparatus for pretreatment for saccharification of lignocellulose biomass of the present invention, the lignocellulose biomass is mixed with ammonia water supplied by the ammonia water supply unit by means of the mixing unit, leading to a biomass-ammonia mixture. Next, the biomass-ammonia mixture is heated by the first heating unit and boiled. In this manner, the biomass is expanded by the expansion effect of the ammonia water by boiling; at the same time, it is treated with alkali of the ammonia water to remove lignin. Thus, the biomass is prevented from inhibition of an enzymatic saccharification reaction by lignin. Furthermore, since the pretreatment apparatus uses ammonia water, treatment can be made by boiling without pressurization and compression. Therefore, the apparatus for pretreatment for saccharification of lignocellulose biomass of the present invention requires no pressurization and compression and thus can easily and continuously treat the biomass.

Furthermore, in the apparatus for pretreatment for saccharification of lignocellulose biomass of the present invention, the biomass-ammonia mixture is heated by the heating unit and boiled. As a result, ammonia evaporates from the biomass-ammonia mixture. In short, ammonia gas is generated. The generated ammonia gas is dissolved in water by the separation unit and recovered as ammonia water. In this manner, the recovered ammonia water can be used directly by the ammonia water supply unit. Thus, the apparatus for pretreatment for saccharification of lignocellulose biomass of the present invention requires no apparatus for liquefying ammonia gas by pressurization and compression. Ammonia water can be reused at low cost.

Furthermore, the apparatus for pretreatment for saccharification of lignocellulose biomass of the present invention preferably has a first heat exchanger which recovers heat from ammonia gas separated by the separation unit, a second heat exchanger which recovers heat from the biomass-water mixture separated by the separation unit, and a heat supply unit which supplies heat recovered from the first and second heat exchangers to the first heating unit. By this configuration, extra heat that the ammonia gas has and extra heat that the biomass-water mixture has are recovered and the recovered heat can be used for heating the biomass-ammonia mixture. Thus, according to the apparatus for pretreatment for saccharification of lignocellulose biomass of the present invention, energy efficiency can be increased.

The heat supply unit may be a third heat exchanger Which exchanges heat with the first heating unit.

Furthermore, the apparatus for pretreatment for saccharification of lignocellulose biomass of the present invention preferably has a second heating unit which heats the biomass-ammonia mixture, between the first heating unit and the ammonia recovery unit. By this configuration, the biomass-ammonia mixture can be further heated to evaporate ammonia contained in the biomass-ammonia mixture without fail.

Furthermore, the apparatus for pretreatment for saccharification of lignocellulose biomass of the present invention preferably has a wet grinding unit between the first heating unit and the second heating unit. By this configuration, the biomass-ammonia mixture is ground by the wet grinding unit; at the same time, heated by heat generated by grinding. As a result, the biomass in the biomass-ammonia mixture is softened by heat due to grinding. By further grinding, lignin constituting the biomass is dissociated from cellulose and removed. Furthermore, by the heat during grinding, ammonia in the biomass-ammonia mixture is evaporated and therefore recovered by the separation unit without fail.

Furthermore, in the apparatus for pretreatment for saccharification of lignocellulose biomass of the present invention, an ammonia concentration of the ammonia water to be supplied to the mixing unit is preferably 5 to 35 wt %. If the ammonia concentration of the ammonia water is less than 5% a sufficient lignin removal effect cannot be often obtained. In contrast, the ammonia concentration of the ammonia water cannot exceed 35 wt % under the atmospheric pressure.

Furthermore, the apparatus for pretreatment for saccharification of lignocellulose biomass of the present invention preferably has an ammonia water returning unit which returns ammonia water recovered by the ammonia recovery unit to the ammonia water supply unit and an ammonia concentration regulation unit which regulates the concentration of the ammonia water to be returned to the ammonia water supply unit. By the configuration, the ammonia water recovered by the separation unit is regulated to have an appropriate ammonia concentration by the ammonia concentration regulation unit and returned by the ammonia water returning unit to the mixing unit for recycle use.

Furthermore, in the apparatus for pretreatment for saccharification of lignocellulose biomass of the present invention, it is preferable that the ammonia water supply unit supplies the ammonia water to the mixing unit such that a mass ratio of the lignocellulose biomass to the ammonia water falls within the range of 1:3 to 1:5. If the mass ratio of the biomass to the ammonia water is less than 1:3, a sufficient lignin removal effect cannot be obtained. In contrast, if the mass ratio of the biomass to the ammonia water exceeds 1:5, ammonia water is excessively present and therefore extra energy is consumed to heat such extra ammonia water.

DESCRIPTION OF EMBODIMENTS

Next, the first embodiment of the present invention will be described.

Figure 1:
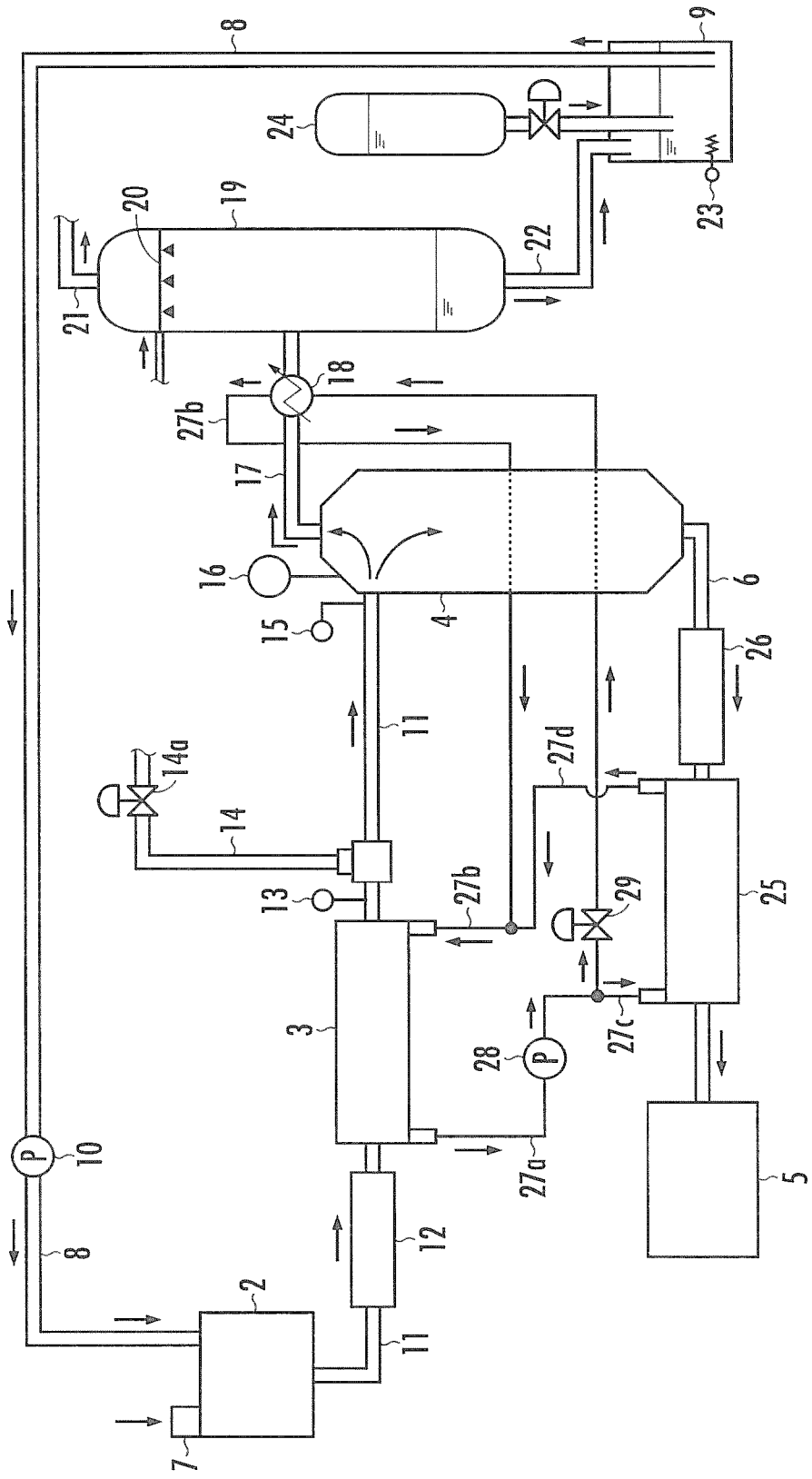
FIG. 1 is a structural view of the system of a pretreatment apparatus for lignocellulose biomass according to a first embodiment.

As shown in FIG. 1, the apparatus 1 for pretreatment for saccharification of lignocellulose biomass according to the first embodiment of the present invention has a mixer 2, a first multitubular heat exchanger 3, a separation tower 4 and a transfer pipe 6 for transferring a separated substance separated by the separation tower 4 to a later step 5.

The mixer 2 has an inlet 7 at the top, for supplying biomass, and has an ammonia water supply pipe 8 connected for supplying ammonia water to be mixed with the biomass. The end of the ammonia water supply pipe 8 on the upstream side is connected to an ammonia tank 9 and has a pump 10 in the middle.

In the lower portion of the mixer 2, a slurry pipe 11 is provided for discharging the slurry. The slurry pipe 11 is connected to the separation tower 4 via the first multitubular heat exchanger 3. The slurry pipe 11 has a slurry pump 12 for feeding the slurry to the first multitubular heat exchanger 3 on the upstream side of the first multitubular heat exchanger 3. Furthermore, to the slurry pipe 11, a first temperature sensor 13 is provided for detecting the temperature of the slurry at the outlet of the first multitubular heat exchanger 3, a vapor pipe 14 is connected on the downstream side of the first temperature sensor 13 and a second temperature sensor 15 is provided for detecting the temperature of the slurry at the inlet of the separation tower 4. The vapor pipe 14 is provided with a flow-rate regulation valve 14a.

In the separation tower 4, the slurry pipe 11 is connected to the upper portion and the transfer pipe 6 is provided to the bottom. Furthermore, to the top portion thereof, a pressure sensor 16 for detecting the pressure within the separation tower 4 and an ammonia gas pipe 17 for discharging separated ammonia gas are provided. The ammonia gas pipe 17 is connected to an absorption tower 19 via the first heat exchanger 18.

The absorption tower 19 has a showering apparatus 20 above the portion at which the ammonia gas pipe 17 is connected. The ammonia gas introduced through the ammonia gas pipe 17 is absorbed by the water showered by the showering apparatus 20 into ammonia water, which is stored in the bottom thereof. The absorption tower 19 has an air vent pipe 21 at the top and an ammonia water discharge pipe 22 at the bottom for discharging the ammonia water. The end of the ammonia water discharge pipe 22 on the downstream side is connected to the ammonia tank 9.

The ammonia tank 9 has an ammonia concentration sensor 23 for detecting the concentration of the ammonia water stored therein and a concentrated ammonia water supply apparatus 24 for supplying concentrated ammonia water to the ammonia tank 9 depending upon the concentration of ammonia water detected by the ammonia concentration sensor 23.

The transfer pipe 6 is connected to the later step 5 via a second multitubular heat exchanger 25. The transfer pipe 6 has a slurry pump 26 on the upstream side of the second multitubular heat exchanger 25, for feeding the biomass-water mixture to the second multitubular heat exchanger 25.

The first heat exchanger 18 provided in the middle of the ammonia gas pipe 17 is connected to the first multitubular heat exchanger 3 by way of a first heat medium pipe 27a and a second heat medium pipe 27b. The first heat medium pipe 27a connects the secondary side of the first multitubular heat exchanger 3 and the primary side of the first heat exchanger 18, whereas the second heat medium pipe 27b connects the secondary side of the first heat exchanger 18 and the primary side of the first multitubular heat exchanger 3.

Furthermore, the first heat medium pipe 27a has a heat medium pump 28. From the pipe 27a, a third heat medium pipe 27c is diverged, which is connected to the primary side of the second multitubular heat exchanger 25 from the downstream side of the heat medium pump 28. The first heat medium pipe 27a has a flow-rate regulation valve 29 downstream of the divergence point of the third heat medium pipe 27c. Onto the secondary side of the second multitubular heat exchanger 25, a fourth heat medium pipe 27d is provided. The fourth heat medium pipe 27d merges into the second heat medium pipe 27b in the middle.

Next, how to operate the apparatus 1 for pretreatment for saccharification of lignocellulose biomass of the embodiment will be described.

In the apparatus 1 for pretreatment for saccharification of lignocellulose biomass of the embodiment, first, biomass is introduced from the inlet 7 to the mixer 2. The biomass is, for example, naturally dried rice straw having a water content of about 10 wt %. The biomass is pulverized into pieces of 3 mm in length by a cutter mill (not shown) and then further pulverized by the dry-system blade mill (not shown) into powder having a cumulative 50% particle size of 140 μm. The biomass is supplied by, for example, a screw feeder (not shown) to the biomass inlet 7.

Next, the ammonia water in the ammonia tank 9 is supplied to the mixer 2 by means of the pump 10 through the ammonia water supply pipe 8. At this time, the concentration of the ammonia water to be supplied to the mixer 2 has been regulated to, for example, 26.8 wt %. The biomass and the ammonia water are supplied at a flow rate of 12 kg/hour and 48 kg/hour respectively to the mixer 2 such that they satisfy a weight ratio of for example, 1:4.

Next, the biomass is mixed with the ammonia water by the mixer 2 to prepare slurry having the biomass dispersed in the ammonia water. The slurry prepared in the mixer 2 is fed to the first multitubular heat exchanger 3 so as to satisfy a flow rate of for example, 60 kg/hour, by means of the slurry pump 1 through the slurry pipe 11. The first multitubular heat exchanger 3 heats the slurry by use of the heat medium supplied from the first heat medium pipe 27b. At this time, the temperature of the heat medium is regulated to be, for example, about 85° C., and the temperature of the slurry detected by the first temperature sensor 13 at the outlet of the first multitubular heat exchanger 3 is regulated to be about 65° C.

Next, the slurry heated by the first multitubular heat exchanger 3 is further heated by water vapor supplied from the vapor pipe 14 and boiled. In this manner, the biomass is expanded by the expansion effect of the ammonia water by boiling and treated with alkali due to the ammonia water to remove lignin. Removal of lignin from the biomass is continued until the slurry is supplied to the separation tower 4 through the slurry pipe 11. The temperature of the water vapor supplied from the vapor pipe 14 is set to be, for example, about 135° C. and the temperature of the slurry detected by the second temperature sensor 15 before the separation tower 4 is set to be about 100° C.

Since the slurry is heated by the first multitubular heat exchanger 3 and the water vapor as described above, when the slurry is supplied to the separation tower 4, ammonia in the slurry evaporates and the slurry is separated into ammonia gas and a biomass-water mixture.

Figure 2:
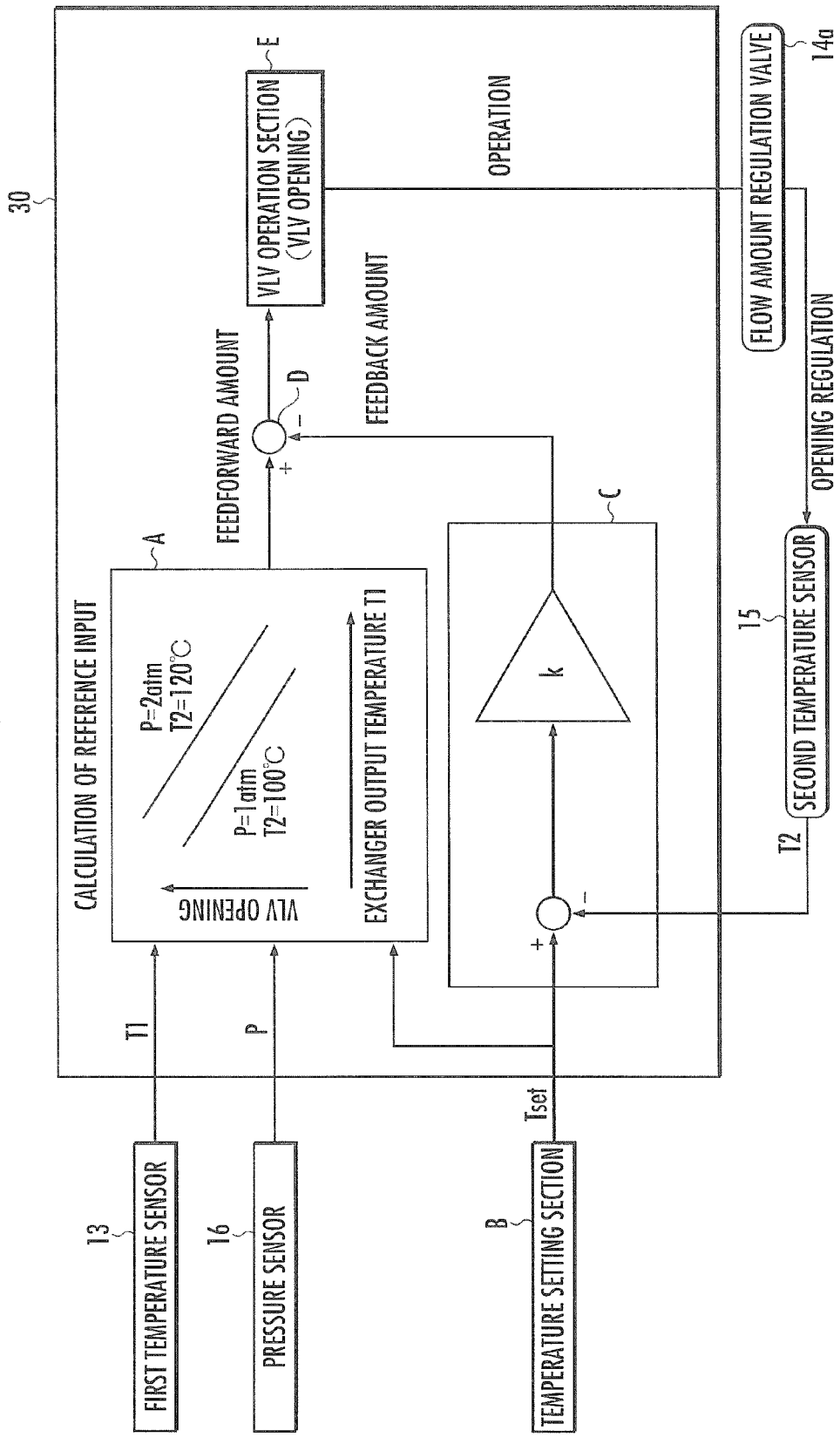
FIG. 2 is a block diagram showing a heating unit for heating lignocellulose biomass by means of a vapor pipe in the apparatus shown in FIG. 1.

The amount of water vapor supplied from the vapor pipe 14 is controlled by a heating control means 30 shown in FIG. 2. In the control means 30, first, in a first arithmetic logical unit A, temperature T1 of the slurry (hereinafter, sometimes simply referred to as a heat exchanger outlet temperature) at the outlet of the first multitubular heat exchanger 3 detected by the first temperature sensor 13 and pressure P within the separation tower 4 detected by a pressure sensor 16 are compared to a temperature setting value $T_{set}$ set by a temperature setting section B. In this manner, a feed forward amount relating to the opening of a flow-rate regulation valve 14a is determined in the first arithmetic logical unit A.

Figure 3:
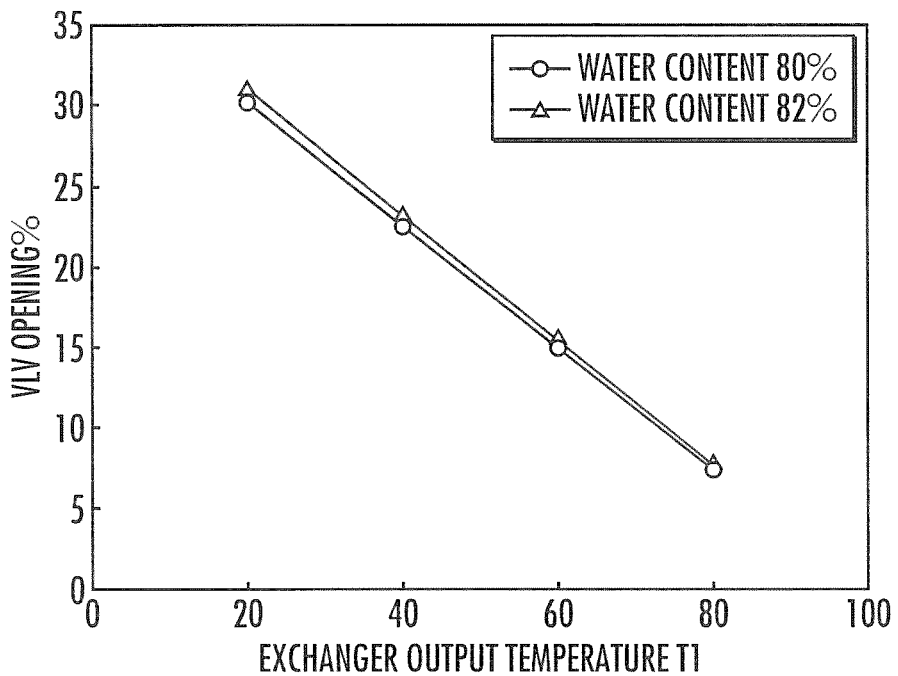
FIG. 3 is a graph showing the relationship between temperature of lignocellulose biomass and the valve opening of the vapor pipe in the heating unit shown in FIG. 2.
Figure 3:
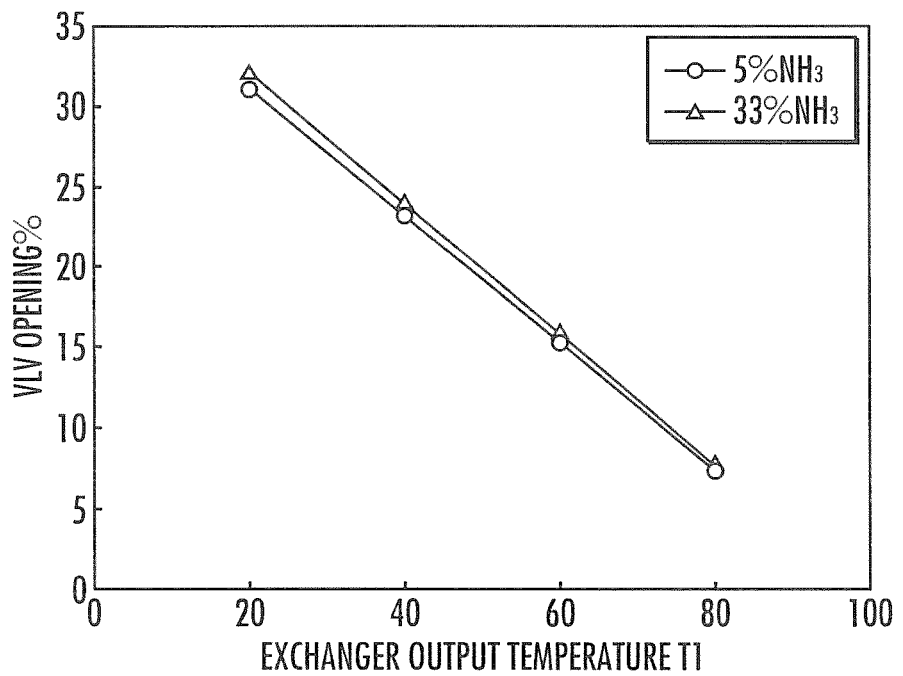

The feedforward amount used herein is calculated based on the relationship shown in, for example, FIG. 3 (a), from heat exchanger outlet temperature T1 depending upon the water content of the slurry. Alternatively, the feedforward amount may be calculated based on the relationship shown in FIG. 3 (b), from the heat exchanger outlet temperature T1 dependent upon the ammonia concentration of the slurry.

As is apparent from FIG. 3 (a) or FIG. 3 (b), the feedforward amount is specifically determined such that if the heat exchanger outlet temperature T1 is high, the opening of the flow-rate regulation valve 14a is reduced, whereas if the heat exchanger outlet temperature T1 is low, the opening of the flow-rate regulation valve 14a is increased.

In contrast, in a second arithmetic logical unit C, temperature T2 of the slurry at the inlet of the separation tower 4 detected by the second temperature sensor 15 is compared to the temperature setting value $T_{set}$ set in the temperature setting section B. The difference k between them is determined as the feedback amount relating to the opening of the flow-rate regulation valve 14a.

The feedforward amount and feedback amount determined as mentioned above are compared and regulated in a comparison section D and a correction value regarding the opening of the flow-rate regulation valve 14a is output to a valve operation section E. As a result, in the valve operation section E, the opening of the flow-rate regulation valve 14a is determined and the slurry is heated. The result of heating the slurry by the aforementioned operation is detected by the second temperature sensor 15 as the inlet temperature T2 of the slurry in the separation tower 4 and further used for determining the feedback amount in the second arithmetic logical unit C.

Next, the ammonia gas separated in the separation tower 4 is supplied to the absorption tower 19 through the ammonia gas pipe 17 and via the first heat exchanger 18. At this time, extra heat of the ammonia gas is recovered by the heat exchanger 18 into the heat medium. The ammonia gas supplied to the absorption tower 19 is absorbed by water showered by the showering apparatus 20 and stored as ammonia water in the bottom of the absorption tower 19. Water is showered by the showering apparatus 20 at a flow rate of, for example, 35.2 kg/hour.

The ammonia water stored in the bottom of the absorption tower 19 is returned to the ammonia tank 9 through the ammonia water discharge pipe 22. In the ammonia tank 9, the concentration of the ammonia water stored therein is detected by the ammonia concentration sensor 23. Concentrated ammonia water is supplied by the concentrated ammonia water supply apparatus 24 depending upon the detected concentration of the ammonia water to regulate, for example, to 26.8 wt %.

Furthermore, the biomass-water mixture separated by the separation tower 4 is transferred by the slurry pump 26 to the later step 5 through the transfer pipe 6. The later step 5 is, for example, a step of performing enzymatic fermentation treatment of cellulose contained in the biomass by supplying a predetermined amount of water and fermentation enzyme to the biomass-water mixture. Note that, extra heat of the biomass-water mixture is recovered by the second multitubular heat exchanger 25 provided to the transfer pipe 6 into the heat medium.

The heat medium is used for heating the slurry in the first multitubular heat exchanger 3 and thereafter discharged from the secondary side thereof and introduced to the primary side of the first heat exchanger 18 by means of the heat medium pump 28 through the first heat medium pipe 27a. The heat medium introduced into the first heat exchanger 18 is then used for recovering heat from the ammonia gas separated by the separation tower 4. Thereafter, the heat medium is discharged from the secondary side of the first heat exchanger 18, passes through the second heat medium pipe 27b and is introduced to the primary side of the first multitubular heat exchanger 3. Furthermore, part of the heat medium passing through the first heat medium pipe 27a is separated therefrom and passes into a third heat medium pipe 27c and introduced to the primary side of the second multitubular heat exchanger 25. Next, the heat medium introduced into the second multitubular heat exchanger 25 is used for recovery of heat from the biomass-water mixture separated by the separation tower 4. Thereafter, the heat medium is discharged from the secondary side of the second multitubular heat exchanger 25, passes through the fourth heat medium pipe 27d and is merged into the second heat medium pipe 27b. The partition ratio of the heat medium of the first heat medium pipe 27a to the third heat medium pipe 27c is regulated by a flow-rate regulation valve 29.

Next, a second embodiment of the present invention will be described.

Figure 4:
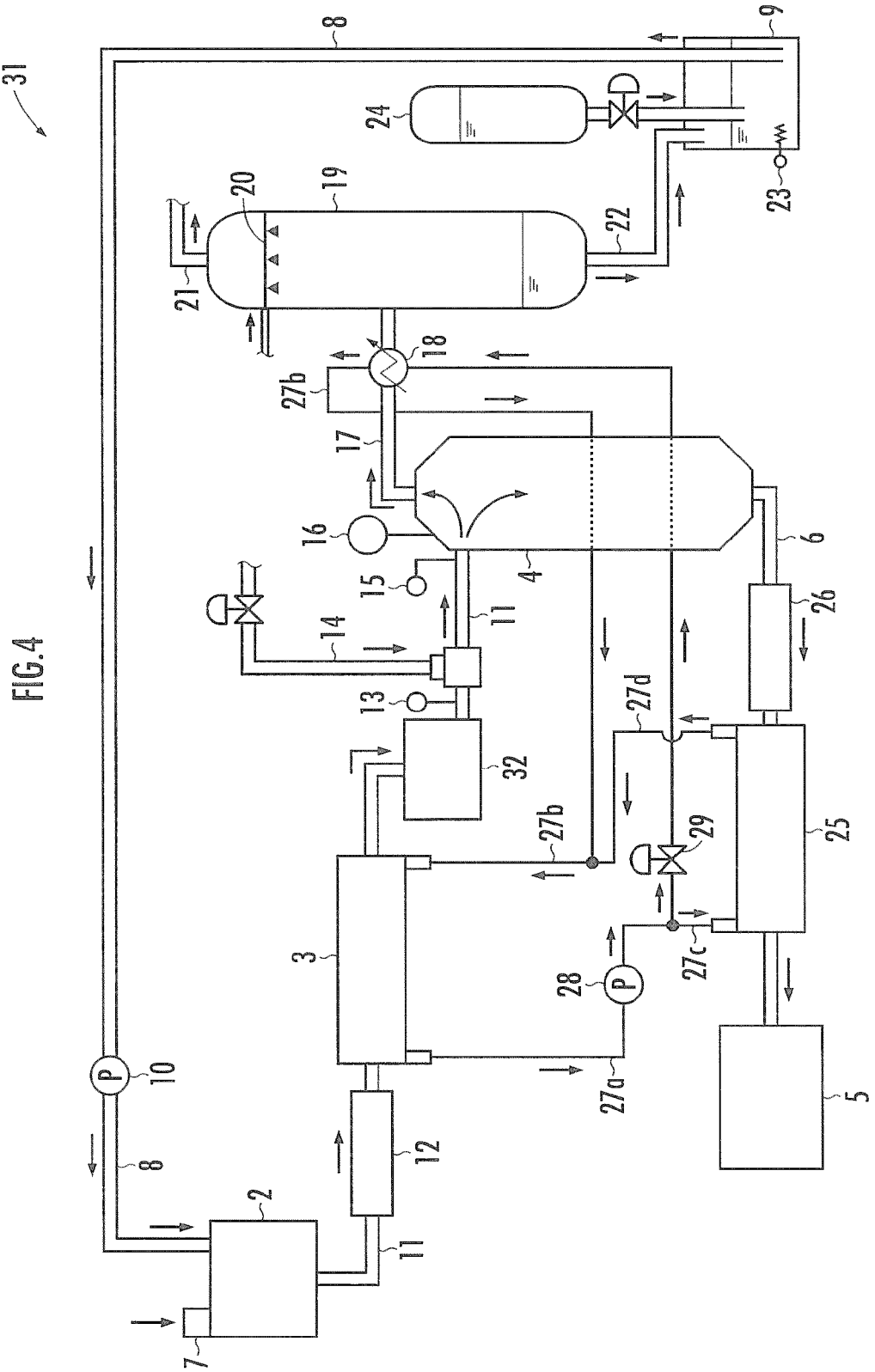
FIG. 4 is a structural view of the system of a pretreatment apparatus for lignocellulose biomass according to a second embodiment.

As shown in FIG. 4, the apparatus 31 for pretreatment for saccharification of lignocellulose biomass according to a second embodiment of the present invention has completely the same structure as that of the apparatus 1 for pretreatment for saccharification of lignocellulose biomass shown in FIG. 1 except that it has a wet type grinder 32 interposed between the first multitubular heat exchanger 3 and the first temperature sensor 13.

Next, how to operate an apparatus 31 for pretreatment for saccharification of lignocellulose biomass of the present embodiment will be described.

The apparatus 31 for pretreatment for saccharification of lignocellulose biomass of the present embodiment is operated in completely the same manner as in the apparatus 1 for pretreatment for saccharification of lignocellulose biomass of the first embodiment except that the slurry is heated by the first multitubular heat exchanger 3 and then ground by the wet-type grinder 32.

The wet-type grinder 32 has a pair of grindstones (not shown) facing each other. The pair of grindstones mutually faces with an interval of, for example, 100 μm between them. The slurry heated by the first multitubular heat exchanger 3 is continuously supplied to the space between the grindstones. Next, while one of the grindstones is immobilized, the other grindstone is rotated at a rotation rate of, for example, 1500 rpm. In this way, the slurry is ground by the grindstones and simultaneously heated with friction heat. Next, the slurry ground is transferred in the circumference direction by centrifugal force and discharged from the space between the grindstones. At this time, the slurry is heated by friction heat generated between the grindstones to about 80° C. Next, the slurry ground is supplied by means of a slurry pump (not shown) to the separation tower 4 through the slurry pipe 11 at the same flow rate as that of the slurry pump 12.

According to the apparatus 31 for pretreatment for saccharification of lignocellulose biomass of the present embodiment, since the slurry can be heated to about 80° C. by the friction heat between the grindstones, the amount of water vapor supplied from the vapor pipe 14 can be reduced. Furthermore, by mechanically pulverizing the biomass in the slurry by the wet-type grinder 32, a fermentation efficiency of enzymatic fermentation performed in the later step 5 can be increased.

Furthermore, according to each of the apparatuses 1, 31 for pretreatment for saccharification of lignocellulose biomass of the embodiments, by virtue of a boiling treatment with ammonia water, the expanding effect on the biomass can be obtained. Since the fibers of the biomass become loosen by the expanding effect, the biomass is susceptible to an enzymatic saccharification treatment performed in the later step 5.

Furthermore, since the ammonia water has a low boiling point, a boiling treatment can be performed at a low temperature. As a result, a fermentation inhibitory substance is rarely generated. Furthermore, since ammonia water can be evaporated, the ammonia water itself can be easily neutralized. Furthermore, even an inhibitory substance, i.e., an acidic organic substance is generated, since the ammonia water is alkali, a neutralization treatment can be easily performed.

Furthermore, each of the apparatuses 1, 31 for pretreatment for saccharification of lignocellulose biomass of the embodiments may have a static mixer within the slurry pipe 11 at the position corresponding to the first multitubular heat exchanger 3 and downstream of the vapor pipe 14. By virtue of this, the slurry can be uniformly heated.

Furthermore, in each of the apparatuses 1, 31 for pretreatment for saccharification of lignocellulose biomass of the embodiments, ammonia concentration in the ammonia tank 9 may be regulated by the concentrated ammonia water supply apparatus 24 at intervals of a predetermined time, for example, every 24 hours.

Furthermore, in each of the apparatuses 1, 31 for pretreatment for saccharification of lignocellulose biomass of the embodiments, ammonia is used for pretreatment for the biomass before saccharification. Therefore, nitrogen may remain in the biomass residue produced in the later step 5. Such a biomass residue can be used in, e.g., a fertilizer.

REFERENCE SIGNS LIST

1, 31 . . . Apparatus for pretreatment for saccharification of lignocellulose biomass,
2 . . . Mixer (mixing unit),
3 . . . First multitubular heat exchanger (first heating unit),
4 . . . Separation tower (separation unit),
5 . . . Later step,
6 . . . Transfer pipe (transfer unit),
8 . . . Ammonia water supply pipe,
14 . . . Vapor pipe (second heating unit),
18 . . . First heat exchanger,
19 . . . Absorption tower (ammonia recovery unit),
22 . . . Ammonia water discharge pipe,
24 . . . Concentrated ammonia water supply apparatus,
25 . . . Second multitubular heat exchanger (second heat exchanger),
27 . . . Heat medium pipe (heat supply unit),
32 . . . Wet-type grinder.

The invention claimed is:

1. An apparatus for pretreatment for saccharification of lignocellulose biomass comprising
a mixing unit which mixes lignocellulose biomass and ammonia,
a first heating unit which heats a biomass-ammonia mixture provided by the mixing unit,
a separation unit which separates ammonia gas from the biomass-ammonia mixture heated by the first heating unit to obtain a biomass-water mixture,
a transfer unit which transfers the biomass-water mixture separated by the separation unit to a later step,
an ammonia water supply unit which supplies ammonia water having an ammonia concentration of 5 to 35 wt % to the mixing unit, and
an ammonia recovery unit which recovers ammonia gas as ammonia water by dissolving ammonia gas separated by the separation unit in water,
a first heat exchanger recovering heat from ammonia gas separated by the separation unit,
a second heat exchanger recovering heat from the biomass-water mixture separated by the separation unit, and
a heat supply unit supplying heat recovered from the first and second heat exchangers to the first heating unit.

2. The apparatus for pretreatment for saccharification of lignocellulose biomass according to claim 1, wherein the heat supply unit is a third heat exchanger which exchanges heat with the first heating unit.

3. The apparatus for pretreatment for saccharification of lignocellulose biomass according to claim 1, comprising a second heating unit which heats the biomass-ammonia mixture between the first heating unit and the separation unit.

4. The apparatus for pretreatment for saccharification of lignocellulose biomass according to claim 1, comprising a second heating unit which heats the biomass-ammonia mixture between the first heating unit and the separation unit, and a wet grinding unit between the first heating unit and the second heating unit.

5. The apparatus for pretreatment for saccharification of lignocellulose biomass according to claim 1, comprising:
an ammonia water returning unit which returns ammonia water recovered by the ammonia recovery unit to the ammonia water supply unit, and an ammonia concentration regulation unit which regulates the concentration of the ammonia water to be returned to the ammonia water supply unit.

6. The apparatus for pretreatment for saccharification of lignocellulose biomass according to claim 1, wherein the ammonia water supply unit supplies the ammonia water to the mixing unit such that a mass ratio of the lignocellulose biomass and the ammonia water falls within the range of 1:3 to 1:5.

* * * * *